US00PP20903P2

(12) United States Plant Patent
Sakazaki

(10) Patent No.: US PP20,903 P2
(45) Date of Patent: Mar. 30, 2010

(54) ***PETUNIA* PLANT NAMED 'USTUNI60-01M'**

(50) Latin Name: *Petunia×hybrida*
Varietal Denomination: USTUNI60-01M

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 12/291,564

(22) Filed: Nov. 12, 2008

(51) Int. Cl.
*A01H 5/00* (2006.01)

(52) U.S. Cl. ..... Plt./356
(58) Field of Classification Search ..... Plt./356
See application file for complete search history.

*Primary Examiner*—Annette H Para
(74) *Attorney, Agent, or Firm*—C. A. Whealy

(57) ABSTRACT

A new and distinct cultivar of *Petunia* plant named 'USTUNI60-01M', characterized by its upright, outwardly spreading and mounding plant habit; freely branching and vigorous growth habit; numerous single flowers that are white in color with red purple-colored venation; and good garden performance.

1 Drawing Sheet

Botanical designation: *Petunia×hybrida.*
Cultivar denomination: 'USTUNI60–01M'.

BACKGROUND OF THE INVENTION

The present invention relates to a new and distinct cultivar of *Petunia* plant, botanically known as *Petunia×hybrida* and hereinafter referred to by the name 'USTUNI60–01M'.

The new *Petunia* plant is a naturally-occurring branch mutation of a *Petunia×hybrida 'USTUNI*6001', disclosed in U.S. Plant Pat. No. 17,730. The new *Petunia* was discovered and selected by the Inventor on a single plant from within a population of plants of 'USTUNI6001' in a controlled greenhouse environment in Carlton, Mich. on May 15, 2006.

Asexual reproduction of the new *Petunia* plant by vegetative cuttings in a controlled greenhouse environment in Carlton, Mich. since May 15, 2006, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USTUNI60–01M'. These characteristics in combination distinguish 'USTUNI60–01M' as a new and distinct cultivar of *Petunia:*

1. Upright, outwardly spreading and mounding plant habit.
2. Freely branching and vigorous growth habit.
3. Numerous single flowers that are white in color with red purple-colored venation.
4. Good garden performance.

Plants of the new *Petunia* differ from plants of the female parent, 'USTUNI6001' primarily in flower color as plants of 'USTUNI6001' have bright pink-colored flowers.

Plants of the new *Petunia* can be compared to plants of 'Kakegawa' S37, disclosed in U.S. Plant Pat. No. 13,984. In side-by-side comparisons, plants of the new *Petunia* differed from plants of 'Kakegawa S37' in the following characteristics:

1. Plants of the new *Petunia* were more vigorous than plants of 'Kakegawa S37'.
2. Plants of the new *Petunia* and 'Kakegawa S37' differed in flower color as plants of 'Kakegawa S37' had lavender pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph at the bottom of the sheet comprises a side perspective view of a typical plant of 'USTUNI60–01M' grown in a container.

The photograph at the top of the sheet is a close-up view of typical flowers of 'USTUNI6001M'.

DETAILED BOTANICAL DESCRIPTION

The aforementioned photographs and following observations, measurements and values describe plants grown in Bonsall, Calif. under commercial practice during the summer and autumn in an outdoor nursery with day temperatures ranging from 18° C. to 38° C. and night temperatures ranging from 13° C. to 24° C. Rooted young plants had been growing for ten weeks when the photographs and description were taken. In the following description, color references are made to The Royal Horticultural Society Colour Chart, 2001 Edition, except where general terms of ordinary dictionary significance are used.

Botanical classification: *Petunia×hybrida* 'USTUNI6001M'.

Parentage: Naturally-occurring branch mutation of *Petunia× hybrida* 'USTUNI6001', disclosed in U.S. Plant Pat. No. 17,730.

Propagation:

*Type.*—Terminal vegetative cuttings.

*Time to initiate roots, summer and winter.*—About 15 days at 20° C. to 22° C.

*Time to develop roots, summer and winter.*—About 20 days at 18° C. to 20° C.

*Root description.*—Fine; white, close to 155D, in color.

*Rooting habit.*—Freely branching.

Plant description:

*Form/habit.*—Annual flowering plant; indeterminate; upright, outwardly spreading and mounding plant habit; vigorous growth habit. Freely branching habit with about six lateral branches and numerous secondary and tertiary lateral branches per plant. Pinching enhances development of lateral branches.

*Plant height.*—About 24 cm.

*Plant diameter* (*area of spread*).—About 49 cm.

*Lateral branches.*—Length: About 46 cm. Diameter: About 4 mm. Internode length: About 1.7 cm. Texture: Pubescent. Color: Close to 146B.

Foliage description:

*Arrangement.*—Alternate before flowering; opposite after flowers develop; simple.

*Length.*—About 5.2 cm.

*Width.*—About 2.7 cm.

*Shape.*—Elliptical.

*Apex.*—Acute.

*Base.*—Attenuate.

*Margin.*—Entire.

*Texture, upper and lower surfaces.*—Pubescent.

*Venation pattern.*—Pinnate, arcuate.

*Color.*—Developing leaves, upper surface: Close to 137A. Developing leaves, lower surface: Close to 146B. Fully expanded leaves, upper surface: Close to 137B; venation, close to 146B. Fully expanded leaves, lower surface: Close to 146B; venation, close to 146C.

*Petioles.*—Length: About 1 cm. Diameter: About 2 mm. Texture, upper and lower surfaces: Pubescent. Color, upper surface: Close to 146C. Color, lower surface: Close to 147C.

Flower description:

*Flower type and habit.*—Single salverform flowers; flowers face mostly upward or outward; axillary. Freely flowering habit, about 12 to 15 flower buds and open flowers per lateral branch.

*Natural flowering season.*—Long day responsive; long flowering period, early spring until frost in the autumn; flowering continuous during this period. Plants begin flowering about four to six weeks after planting rooted cuttings.

*Flower longevity on the plant.*—About three to five days; flowers persistent.

*Fragrance.*—Faint; sweet, floral.

*Flower size.*—Diameter: About 4.6 cm. Depth (height): About 4.2 cm. Tube length: About 3.2 cm. Throat diameter, distal end: About 1 cm. Tube diameter, proximal end: About 3 mm.

*Flower buds.*—Length: About 2.7 cm. Diameter: About 7 mm. Shape: Columnar. Color: Towards the apex, close to NN155D; towards the base, close to 145C.

*Petals.*—Quantity/arrangement: About five petals fused in a single whorl, funnelform. Length from throat: About 2 cm. Width: About 2.1 cm. Shape: Roughly fan-shaped. Apex: Broadly acute with a central rounded point. Margin: Entire. Texture, upper and lower petal lobe surfaces: Smooth, glabrous; velvety. Throat texture: Smooth, glabrous. Tube texture: Pubescent. Color: When opening, upper and lower surfaces: Close to NN155D. Fully opened, upper surface: Close to N155D; venation, towards the throat, close to 58A; venation, towards the apex, close to 145D. Fully opened, lower surface: Close to N155D; venation, close to 145A. Flower throat (inside): Close to 145C; venation, towards the petal lobes, close to 58A; towards the corolla base, close to 145A. Flower tube (outside): Close to 145A; venation, close to 146C.

*Sepals.*—Arrangement/appearance: Single whorl of five sepals fused at base, star-shaped calyx. Length: About 1.3 cm to 1.5 cm. Width: About 2.5 mm. Shape: Ligulate. Apex: Rounded. Margin: Entire. Texture, upper and lower surfaces: Pubescent. Color, upper surface: Close to 146A. Color, lower surface: Close to 146B.

*Peduncles.*—Length: About 5.2 cm. Width: About 1.5 mm. Angle: About 45° to 60° from the stem axis. Strength: Strong. Texture: Pubescent. Color: Close to 146B.

*Reproductive organs.*—Stamens: Quantity per flower: Five. Anther shape: Oval. Anther size: About 2 mm by 2.5 mm. Anther color: Close to 198C. Pollen amount: Moderate. Pollen color: Close to 188B. Pistils: Quantity per flower: One. Pistil length: About 2 cm. Style length: About 1.8 cm. Style color: Close to 194C. Stigma shape: Oval to anvil-shaped. Stigma color: Close to 194A. Ovary color: Close to 145A.

*Seed/fruit.*—Seed and/or fruit production has not been observed.

Pathogen/pest resistance: Plants of the new *Petunia* have not been noted to be resistant to pathogens or pests common to *Petunia*.

Garden performance: Plants of the new *Petunia* have been observed to have good garden performance. Plants of the new *Petunia* have been noted to tolerate temperatures from about 0° C. to about 38° C. and have excellent tolerance to rain and wind.

It is claimed:

1. A new and distinct *Petunia* plant named 'USTUNI60–01M' as illustrated and described.

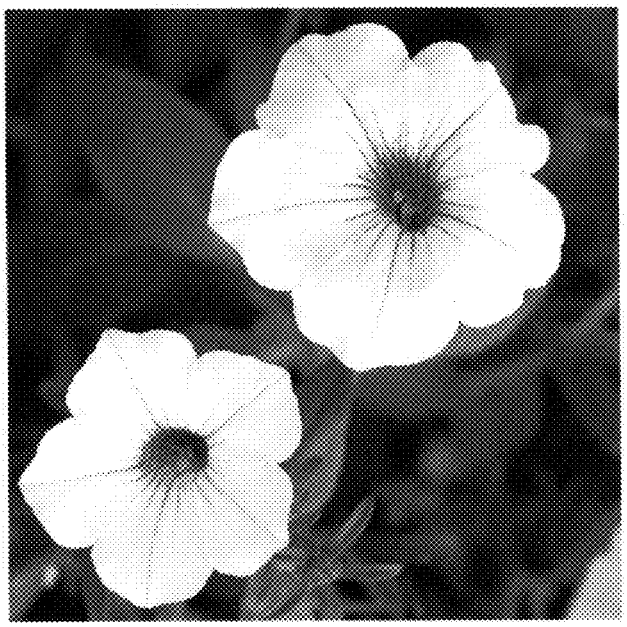
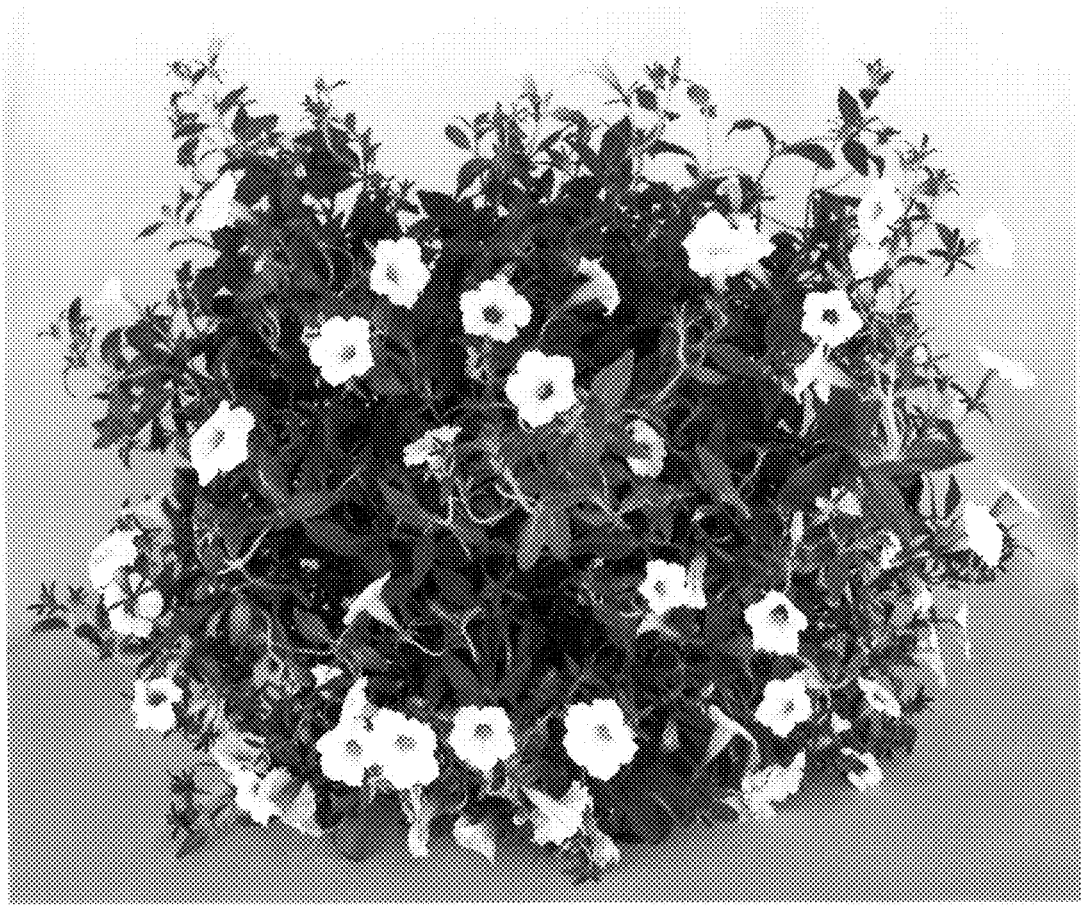

* * * * *